(12) United States Patent
Dijkstra et al.

(10) Patent No.: US 11,247,068 B2
(45) Date of Patent: Feb. 15, 2022

(54) SYSTEM AND METHOD FOR PROVIDING LIGHT THERAPY TO A USER BODY

(71) Applicant: ShenZhen Kaiyan Medical Equipment Co, LTD, Shenzhen (CN)

(72) Inventors: Alain Dijkstra, Amstelveen (NL); Jonathan James Knight, Kent (GB); Jooeun Kim, Seoul (KR); Yong Zhang, Changde (CN); Dan Xu, Shenzhen (GD)

(73) Assignee: ShenZhen Kaiyan Medical Equipment Co, LTD, Shenzhen (CN)

( * ) Notice: Subject to any disclaimer, the term of this patent is extended or adjusted under 35 U.S.C. 154(b) by 107 days.

(21) Appl. No.: 16/150,023

(22) Filed: Oct. 2, 2018

(65) Prior Publication Data
US 2019/0030359 A1 Jan. 31, 2019

(51) Int. Cl.
*A61N 5/06* (2006.01)
*A61B 5/01* (2006.01)
(Continued)

(52) U.S. Cl.
CPC .......... *A61N 5/0616* (2013.01); *A61B 5/0064* (2013.01); *A61B 5/0075* (2013.01); *A61B 5/015* (2013.01); *A61B 5/02055* (2013.01); *A61B 5/441* (2013.01); *A61B 5/442* (2013.01); *A61B 5/444* (2013.01); *A61B 5/445* (2013.01); *A61B 5/7264* (2013.01); *A61N 5/062* (2013.01); *A61N 5/067* (2021.08); *A61N 5/0621* (2013.01); *A61N 5/0624* (2013.01); *A61N 2005/0626* (2013.01); *A61N 2005/0652* (2013.01);
(Continued)

(58) Field of Classification Search
USPC .......................................................... 607/89
See application file for complete search history.

(56) References Cited

U.S. PATENT DOCUMENTS 6,416,476 B1 * 7/2002 Ogasawara .............. A61B 8/00
600/425
6,887,260 B1 * 5/2005 McDaniel ............ A61B 18/203
607/88
(Continued)

OTHER PUBLICATIONS

Maria I. Davila The PhysioCam: A Novel Non-Contact Sensor to Measure Heart Rate Variability in Clinical and Field Applications https://www.ncbi.nlm.nih.gov/pmc/articles/PMC5702637/.

*Primary Examiner* — Tammie K Marlen
*Assistant Examiner* — Michael J Lau
(74) *Attorney, Agent, or Firm* — Emanus, LLC; Willie Jacques

(57) ABSTRACT

The invention provides a light therapy device for providing therapeutic treatment to a user's body, wherein the user may be a person or an animal. The device is using a light projection method for treating the body problems and/or skin disorders. Further, the device is having a rotatable assembly that automatically follows the movement of the desired area of the body needs to be treated. The device uses artificial intelligence, machine learning, localization modules, object detection module, image processing module, and 3D-mapping to automatically identify and treating the desired area of the body. Furthermore, the user can manually identify, select and prioritize desired treatment portion and can select the type of treatment required.

20 Claims, 10 Drawing Sheets

(51) Int. Cl.
  *A61B 5/00* (2006.01)
  *A61B 5/0205* (2006.01)
  *A61N 5/073* (2006.01)
  *A61N 5/067* (2006.01)

(52) U.S. Cl.
  CPC .............. *A61N 2005/0654* (2013.01); *A61N 2005/0661* (2013.01); *A61N 2005/073* (2013.01)

(56) References Cited

U.S. PATENT DOCUMENTS

| | | | | |
|---|---|---|---|---|
| 9,980,649 B1* | 5/2018 | Abedini | ................ | H04N 7/181 |
| 2005/0143793 A1* | 6/2005 | Korman | ............... | A61N 5/0616 |
| | | | | 607/94 |
| 2005/0154381 A1* | 7/2005 | Altshuler | ............... | A61B 18/20 |
| | | | | 606/9 |
| 2005/0278004 A1* | 12/2005 | Steinert | ............... | A61F 9/00802 |
| | | | | 607/89 |
| 2006/0095099 A1* | 5/2006 | Shanks | ................ | A61N 5/0617 |
| | | | | 607/89 |
| 2006/0253176 A1* | 11/2006 | Caruso | ................ | A61B 18/203 |
| | | | | 607/88 |
| 2008/0103563 A1* | 5/2008 | Powell | ................ | A61N 5/0616 |
| | | | | 607/89 |
| 2008/0194928 A1* | 8/2008 | Bandic | ................... | A61B 5/442 |
| | | | | 600/306 |
| 2008/0267814 A1* | 10/2008 | Bornstein | ................ | A61N 5/06 |
| | | | | 422/22 |
| 2010/0082019 A1* | 4/2010 | Neev | .................... | A61B 18/203 |
| | | | | 606/9 |
| 2011/0213446 A1* | 9/2011 | Tucek | ................. | A61N 5/0616 |
| | | | | 607/89 |
| 2011/0224759 A1* | 9/2011 | Shanks | ................ | A61N 5/0616 |
| | | | | 607/89 |
| 2012/0029417 A1* | 2/2012 | Samain | ................ | A61N 5/0616 |
| | | | | 604/20 |
| 2013/0060134 A1* | 3/2013 | Eshima | .................... | A61B 6/12 |
| | | | | 600/431 |
| 2013/0188779 A1* | 7/2013 | Chao | ....................... | A61B 8/085 |
| | | | | 378/150 |
| 2013/0245459 A1* | 9/2013 | Qu | ....................... | A61B 5/1032 |
| | | | | 600/476 |
| 2014/0267662 A1* | 9/2014 | Lampo | .................. | G16H 50/70 |
| | | | | 348/77 |
| 2015/0148684 A1* | 5/2015 | Baym | ................. | A61B 5/0071 |
| | | | | 600/476 |
| 2015/0224340 A1* | 8/2015 | Ajiki | .................... | A61N 5/0617 |
| | | | | 607/90 |
| 2016/0354058 A1* | 12/2016 | Schlosser | ............. | A61B 8/4461 |
| 2017/0156662 A1* | 6/2017 | Goodall | ............... | G16H 50/30 |
| 2017/0326385 A1* | 11/2017 | Fishman | .............. | A61B 8/0858 |
| 2018/0014777 A1* | 1/2018 | Amir | ..................... | A61B 5/443 |
| 2018/0193186 A1* | 7/2018 | Wright | .................. | A61F 7/0085 |
| 2018/0234603 A1* | 8/2018 | Moore | ............... | H04N 5/23245 |
| 2018/0303343 A1* | 10/2018 | Dubin | .................. | A61B 5/7285 |
| 2019/0038353 A1* | 2/2019 | Fatemi | ................ | A61N 5/0616 |

\* cited by examiner

SYSTEM AND METHOD FOR PROVIDING LIGHT THERAPY TO A USER BODY

FIELD OF THE INVENTION

The present disclosure relates to a system, method, and device for providing light therapy to a user. More particularly, the device for treating various external and internal body conditions by using LED Light Therapy, Laser Light Therapy, Photo-Bio-Modulation Therapy (PBMT), Photodynamic Therapy (PDT), UV based light therapy and/or any other suitable light therapy.

DESCRIPTION OF THE BACKGROUND ART

Skin is the largest organ of the human body. Due to continuous exposure to the outside environment or due to genetic makeup, our skin is prone to diseases such as allergy, inflammation, dermatitis, hives, acnes, redness, irritants, itching, swelling, sebaceous, pimples and other skin disorders. There are several known techniques, attempting to reduce or eliminate the skin abnormalities or to diagnose skin disorders.

Such treatments include antimicrobials such as, Benzoyl Peroxide which kill or inhibit growth of the bacteria playing role in acne growth; sebum modulating agents such as Retinoid, including Tretinoin and Isotretinoin which influence sebum production; Keratolytic agents such as salicylic acid which accelerate cell turnover and open hair follicles; anti-inflammatories such as Dimethyl Amino Ethanol (DMAE) to reduce redness and pain associated with acne lesions; cleansing agents such as alcohols to open the infundibulum and allow free sebum exit to the skin surface; anti-spot/pigmentation agents such as ascorbic acid to prevent or treat pigmentation and color contrast on the skin, and anti-scar agents such as copper peptides to reduce the impact of scar formation from acne lesions. Further, rosacea can be treated with antibiotics, sulfur, sodium sulfacetamide, and retinoid.

Numerous other techniques are also proposed to provide cosmetic and/or anti-aging or skin rejuvenation benefits. For example, it has been proposed to expose the skin to electromagnetic radiation. The electromagnetic radiation typically includes wavelengths that are absorbed by at least one chromophore present in the skin, (e.g. melanin, hemoglobin) such that the incident energy can be converted to heat. If sufficient energy is delivered and absorbed, one or more benefits such as age spot reduction, mottled hyperpigmentation reduction, wrinkle reduction, blood vasculature reduction, reduction of skin roughness, and lifting of sagging skin may be imparted to the skin.

Certain light spectrums emitted by LEDs (blue or red) are known to be therapeutic for skin treatment against maladies such as acne and are beneficial to inhibit skin aging.

In the US patent No. 2012,002,941,7A1 Henri Samain et. al discloses a treatment method for treating human keratinous material, the method comprising: a) projecting an image onto a zone to be treated; b) modifying the content and/or adjusting the projected image; and c) cosmetically treating the zone as a function of the image as modified and/or adjusted in this way.

In U.S. Pat. No. 6,887,260B1, David H. McDaniel discloses a system and method for treatment of skin disorders. More particularly, the disclosed invention is directed toward the treatment of acne and acne scarring by treating sebaceous oil glands and the surrounding tissue with an exogenous chromophore composition and then exposing the target tissue to visible, infrared, or ultraviolet light to inhibit the activity of the oil gland and eliminate acne bacteria. The treatment method of the present invention may be further augmented by enhancing the penetration of the topical composition into the oil gland and surrounding tissue through the use of procedures including enzyme peeling, abrasion, or ultrasound.

In another US Patent Application No. 2008,010,356,3A1 Steven D. Powell et. al discloses a personal care device comprising a phototherapy component and a microdermabrasion component. The phototherapy device component may comprise an array of light emitting diodes (LEDs), which are configured to emit light over a range of wavelengths which are selected to treat a skin disorder. The LED array may be disposed behind the exfoliating surface of the microdermabrasion component so light therapy treatment and microdermabrasion treatment may be performed simultaneously.

The basic premise of light-based treatment is that different wavelength trigger different reactions beneath the epidermis and penetrate the skin at varying depths. Blue light is generally used to kill the bacteria that causes acne, providing an effective treatment for blackheads and whiteheads, whereas wavelengths of red light are normally used to speed up healing and stimulate collagen production, simultaneously shrinking enlarged pores and tightening the skin.

However, it is still desirable to have a convenient at-home skin treatment device that is portable, lightweight and that is simple to use without user discomfort. Currently available at-home, consumer usable products on the market are fixed to one-size and/or usually have to be hand-held and the user has to manually target the application area which is cumbersome at times. Further, the available devices are generally not proven satisfactory for providing the best or desired light dispersion. The alternative is customers visiting a doctor's office to receive treatments which is neither affordable nor convenient.

Furthermore, it is also desirable to have a device that can provide full body treatment by using different type of light therapies according to internal and external body conditions or diseases e.g. skin disorders, blood flow, cellular repair, photosensitizer, erectile dysfunction, muscle repair, wound pain, joint pain, nose allergy, hair treatment etc.

BRIEF SUMMARY OF THE INVENTION

Light therapy or phototherapy consists of exposure to daylight or to specific wavelengths of light using polychromatic polarized light, lasers, light-emitting diodes, fluorescent lamps, dichroic lamps or very bright full-spectrum light etc. In this, the light is administered for a prescribed amount of time and intensity on an application surface.

The present disclosure provides a portable, easy to use light therapy device to a user for partial or full body treatment, wherein the light therapy device is being used by a natural person or can be used on animals as well. The light therapy device uses light projection method to treat various type of internal and external body conditions and/or skin disorders. e.g. acne, marks, wound, allergy, skin cancer, inflammation, dermatitis, hives, redness, irritants, itching, swelling, sebaceous, pimples, erectile dysfunction, blood flow, cellular repair, allergy, jaundice, herpes etc.

Further, the light therapy device having a plurality of applications, including but not limited to, the treatment of acne, marks, pimples, hives cellular improvement, blood flow, erectile dysfunction, and other body disorders. Further, the present light therapy device delivers light energy by means of a light source when placed in the proximity of the user.

According to an aspect of the present disclosure, the light therapy device comprising a camera unit, a controlling unit, a display unit, a memory unit, and a light projection unit. Further, the controlling unit is operably connected to the camera unit, the display unit, the memory unit, and the light projection unit. The controlling unit includes a processor which is adapted to execute computer implemented code and software applications stored in the memory unit to perform various functions and control the functionality of the camera unit, the display unit, and the light projection unit.

The camera unit is scanning a user body by using a camera and capturing an image data of a treatment portion of the user body. The camera unit is having sensors to collect various body parameter of the user body i.e. temperature of the user body, type of body condition (external body condition or internal body condition), blood flow and other parameter. Further, the image data and the body parameters are stored in the memory unit. The memory unit is having a database that includes a pre-stored data related to various skin or body conditions, treatment profile and user profile. The controlling unit by utilizing an artificial intelligence module, localization module, image processing module, localization module and object detection module to identify the image data and body parameters of the user body. Furthermore, the controlling unit retrieves the pre-stored data from the memory unit and compare the image data and the body parameters with the pre-stored data, based on the comparison the controlling unit identifies a treatment portion from the image data and also identifies an external body condition and/or an internal body condition from the identified treatment portion. Further, the controlling unit with the help of the artificial intelligence module, localization module, image processing module and object detection module retrieves the similar treatment profile from the database and allows the light projection unit to project a light on the external body condition and/or the internal body condition of the user body based on an treatment information stored in the treatment profile.

According to another aspect of the present disclosure, a light therapy system is having two or more light therapy devices to provide maximum or full body treatment with minimum user intervention and body movement. The two or more light therapy devices are placed in the proximity of the user in such a way that they cover a maximum portion of the user body. Further, the two or more light therapy devices automatically allocate their separate treatment portions so that they do not overlap each other's treatment portion while the light is being projected on the allocated treatment portion by the two or more light therapy devices.

According to yet another aspect of the present disclosure, the camera is a normal optical camera, a thermographic camera, an infrared spectroscopy camera, and an IP camera. Further, the sensors used in the light therapy device are non-contact type sensors, IR sensors, temperature sensors, thermal imaging sensors, ultrasonic and infrared sensors. Further, the plurality of sensors is selected from a group of physical contact sensors and non-physical contact sensors. The plurality of sensors is not limited to Infra-red temperature sensor, proximity sensor, ultrasonic sensor, non-contact sensors that utilize videography, the light sensor embedded in the camera limits the quality of the pulse signal as described in "The PhysioCam: A Novel Non-Contact Sensor to Measure Heart Rate Variability in Clinical and Field Applications" by Maria I. Davila, Gregory F. Lewis, and Stephen W. Porges.

According to yet another aspect of the present disclosure, the light projection unit includes a light direction controller, a light head and a light source, wherein the light source is a laser light, LEDs, photoreactive chemical producing light, phosphorus or any other suitable light source generating the light ranging from 100-1600 nm wavelength.

According to yet another aspect of the present disclosure, the light direction controller uses techniques like saccade mirror, direction tuning film, laser sintering, or mirror type galvanometer etc. for controlling a direction of the light emitted from the light source.

According to yet another aspect of the present disclosure, the light therapy device further comprises a wired or wireless (NFC, Wi-Fi, Bluetooth) communication means to connect with a remote device for displaying the image data, the treatment portion of the user body, the external body condition, the internal body condition and the treatment information, wherein, the remote device is adapted to send input to the controller unit via communication means.

According to yet another aspect of the present disclosure, the external body condition is skin disorder, skin condition, skin cancer, aged skin, dead skin, sun tanning, wounds, allergy, inflammation, dermatitis, hives, marks, acne, redness, irritants, itching, swelling, sebaceous, lesions pimples, or wrinkles etc.

According to yet another aspect of the present disclosure, the internal body condition is blood flow, fever, erectile dysfunction, joints pain, muscles pain, grey hair, hair fall, eyebrows, cellular improvement, sleep disorder, jaundice, cancer, or any other internal body problems.

According to yet another aspect of the present disclosure, the controlling unit analyzes a refractive index of at least one treatment portion of the user body and projects the light based on the refractive index of the at least one treatment portion of the user body, wherein the controlling unit adjusts a focus of a light on the at least one treatment portion of the user body based on the refractive index of the at least one treatment portion of the user body in order to avoid falling of brightness and reflective light on a user's eyes.

According to yet another aspect of the present disclosure, the treatment portion of the user body includes a face, hand, head, genital area, full body and any specific body portion having at least one external body condition and/or at least one internal body condition.

According to yet another aspect of the present disclosure, the light therapy device allows the user to select a type of treatment, treatment time, intensity of light projection and shape of a light projection based on his/her body condition.

According to yet another aspect of the present disclosure, the light projection unit, the camera unit, the memory unit, and the controlling unit are configured to mount on a rotatable head, wherein the rotatable head synchronously rotates in a direction of movement of at least one treatment portion of the user body. Further, a rotation unit comprises a motor and a spindle connected to the rotation head for rotating the rotation head in all directions. Furthermore, the light projected from the light head continuously follows the at least one treatment portion of the user body within a predefined distance.

According to yet another aspect of the present disclosure, a light therapy provided form the light therapy device is a LED light therapy, laser light therapy, Photo-bio-modulation therapy (PBMT), Photodynamic Therapy (PDT), UV based light therapy or any other suitable light therapy.

According to yet another aspect of the present disclosure, a power unit is also mounted inside the device to provide power to the rotation unit, camera unit, light projection unit, controlling unit, the memory unit, and the display unit. The power unit includes a rechargeable battery, a direct plug-in for household power socket, USB charging or any other suitable power supply means.

According to yet another aspect of the present disclosure, the light therapy system has a remote device connected to the light therapy device via wired or wireless (NFC, Bluetooth, Wi-Fi) connection means. Further, the remote display device is a mobile phone, laptop, desktop, computer, remote control or any other suitable display means, capable of displaying the image data from the camera unit and allows the user to provide inputs to the controlling unit.

According to the yet another aspect of the present disclosure, the light therapy device uses Photo-bio-modulation Therapy (PBMT) known as Low-Level Laser Therapy (LLLT). LLLT is used to improve tissue repair, reduce pain and inflammation wherever the beam is applied on the application surface.

According to yet another aspect of the present disclosure, the light therapy device uses photodynamic therapy (PDT) that uses special drugs, called Photosensitizing agents, along with light to kill cancer cells.

According to yet another aspect of the present disclosure, the light therapy device provides a LED light-based treatment which is a painless, relaxing, and non-invasive skincare treatment, that has multiple benefits particularly stimulating collagen and requires no downtime. Further, the LED treatments work by using an array of bright light-emitting diodes that send low-level light energy into the deeper layers of the skin.

According to yet another aspect of the present disclosure, the light therapy device uses infrared light which tends to be used to treat wrinkles and other problems caused by poor skin support, such as translucent skin or coarse skin.

According to yet another aspect of the present disclosure, the light therapy device uses laser treatment for diagnosing TMJ (Temporomandibular Joint Dysfunction). In this, the light photons (energy) penetrates deep into the tissues surrounding the temporomandibular joint as well as the joint itself. Laser energy decreases inflammation deep in the tissues that produce almost immediate relief stimulating healing.

According to another aspect of the present disclosure, the light therapy device uses infrared light to treat high fever and other allergic rhinitis symptoms such as a runny nose, itching, and sneezing. The devices emit infrared light with a specific wavelength into the nasal cavity, which makes the nasal mucous membranes less sensitive to triggers such as, pollen of flowering plants and trees or other allergens.

According to yet another aspect of the present disclosure, the light therapy device emits a light energy, preferably at a wavelength of 800-1072 nanometers applied to the genitalia area of male/female humans and animals to treat erectile dysfunction. The light causes the release of nitric oxide into the erectile genitalia tissue, and the nitric oxide causes the smooth erectile tissue to relax and engorge, thereby helps the user to get erections.

The foregoing has outlined rather broadly, features and technical advantages of the present invention in order, that the detailed description of the invention that follows may be better understood. Additional features and advantages of embodiments of the invention will be described hereinafter which form the subject of the claims of the invention. The conception and specific embodiment disclosed herein may be readily utilized as a basis for modifying or designing other structures for carrying out the same or similar purposes of the present invention. Please note that such equivalent constructions do not depart from the scope of the invention as set forth in the appended claims. The novel features which are characteristic of the invention, both as to its organization and method of operation, together with further objects and advantages, will be better understood from the following description when considered in connection with the accompanying figures. Each of the figures is provided for the purpose of illustration and description only and is not intended as a limitation of the scope of the present invention or appended claims.

DETAIL DESCRIPTION OF THE DISCLOSURE

Figure 1:
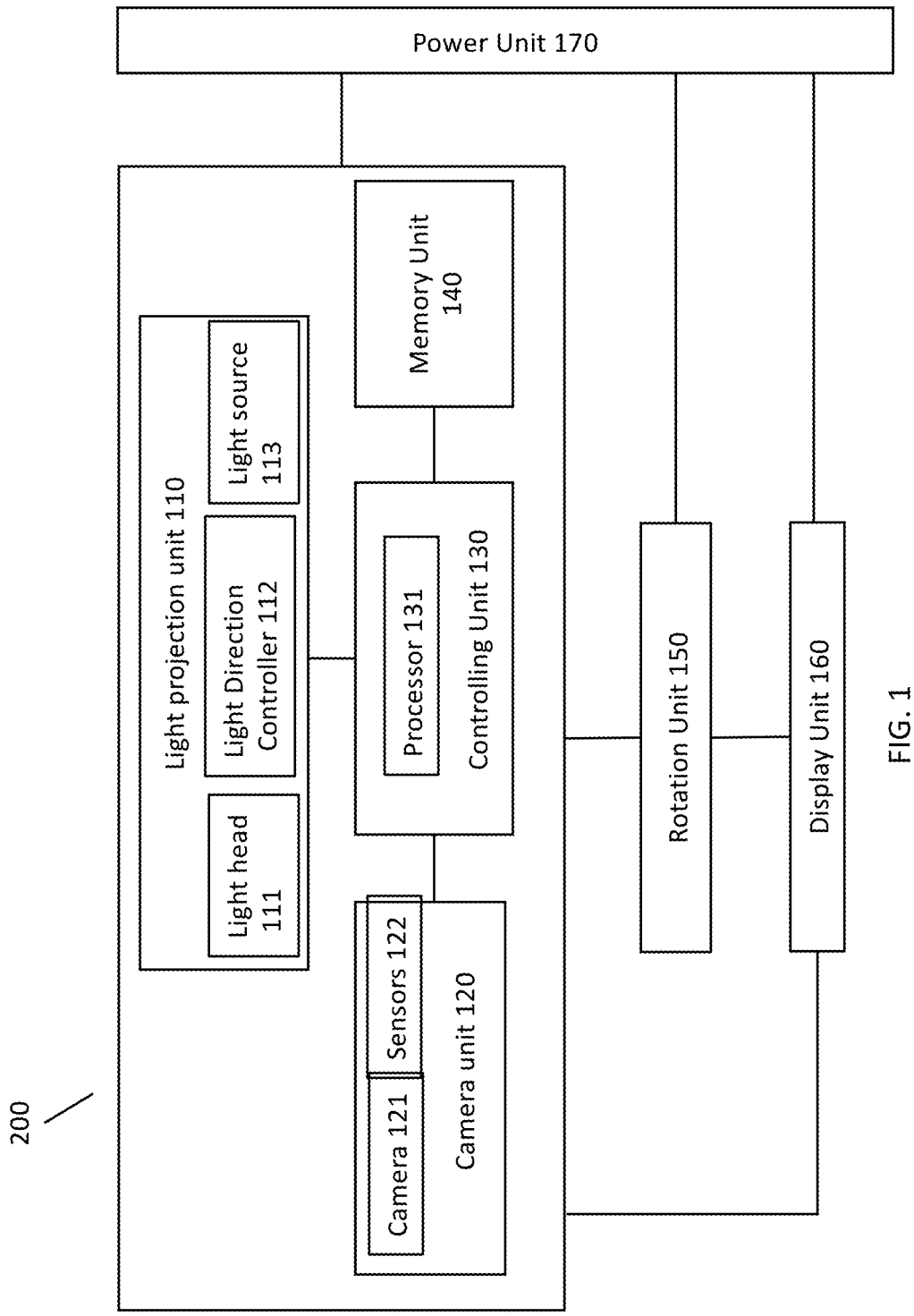
FIG. 1 Shows a block diagram of the components of a light therapy device according to an embodiment of the present disclosure.

Embodiments of the present disclosure will be described more fully hereinafter with reference to the accompanying drawings in which like numerals represent like elements throughout the figures, and in which example embodiments are shown.

The detailed description and the drawings illustrate specific exemplary embodiments by which the invention may be practiced. These embodiments are described in sufficient detail to enable those skilled in the art to practice the invention. It is understood that other embodiments may be utilized, and other changes may be made, without departing from the spirit or scope of the present invention. The following detailed description is therefore not to be taken in a limiting sense, and the scope of the present invention is defined by the appended claims. Embodiments of the claims may, however, be embodied in many different forms and should not be construed as limited to the embodiments set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

From reading the present disclosure, other variations and modifications will be apparent to persons skilled in the art. Such variations and modifications may involve equivalent and other features which are already known in the art, and which may be used instead of or in addition to features already described herein.

Features which are described in the context of separate embodiments may also be provided in combination in a single embodiment. Conversely, various features which are, for brevity, described in the context of a single embodiment, may also be provided separately or in any suitable sub combination. The Applicants hereby give notice that new Claims may be formulated to such features and/or combinations of such features during the prosecution of the present application or of any further application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

A "processor" is capable of accepting a structured input, processing the structured input according to prescribed rules, and producing results of the processing as output. Examples of a processor may include an apparatus that may accept data, process data according to one or more stored software programs, generate results, and typically include input, output, storage, arithmetic, logic, and control units.

"Software" may refer to prescribed rules to operate a computer. Examples of software may include: code segments in one or more computer-readable languages; graphical and or/textual instructions; applets; pre-compiled code; interpreted code; compiled code; and computer programs.

A "computer system" may refer to a system having one or more computers, where each computer may include a computer-readable medium embodying software to operate the computer or one or more of its components. Examples of a computer system may include: a distributed computer system for processing information via computer systems linked by a network; two or more computer systems connected together via a network for transmitting and/or receiving information between the computer systems; a computer system including two or more processors within a single computer; and one or more apparatuses and/or one or more systems that may accept data, may process data in accordance with one or more stored software programs, may generate results, and typically may include input, output, storage, arithmetic, logic, and control units.

In a similar manner, the term "processor" may refer to any device or portion of a device that processes electronic data from registers and/or memory to transform that electronic data into other electronic data that may be stored in registers and/or memory. A "computing platform" may comprise one or more processors.

Referring to FIG. 1 shows a block diagram of components of a light therapy device 200 according to an embodiment of the present disclosure. Further, referring to FIG. 1 and FIG. 2, the light therapy device 200 is having a first housing 210 mounted on a second housing 220. The first housing 210 includes a rotatable head 250 that is mounted on a spindle 230 in a rotatable manner. Further, the rotatable head 250 includes a light projection unit 110, a camera unit 120, a controlling unit 130 and a memory unit 140. Furthermore, the light projection unit 110, the camera unit 120, and the memory unit 140 are electronically and communicatively connected to the controlling unit 130.

The second housing 220 is including a rotation unit 150, a display unit 160, and a power unit 170. A first end 231 of the spindle 230 is connected to a motor mounted inside the rotation unit 150 and a second end 232 of the spindle 230 is connected to the rotatable head 250. Further, the motor rotates the spindle 230 as per the controlling unit 130 input.

The light projection unit 110 is having a light head 111, a light direction controller 112, and a light source 113. In this, the light source 113 projects a light on the light direction controller 112 which is able to control and divert the light as per the controlling unit 130 input. Further, the light direction controller 112 uses saccade mirror, direction tuning film, laser sintering, or mirror type galvanometer etc. techniques for controlling a direction of a light emitted from the light source 113.

The controlling unit 130 is having a processor 131 in order to control the light projecting unit 110, the memory unit 140, the rotation unit 150, the camera unit 120 and the display unit 160.

According to another embodiment of the present disclosure, the light source 113 may be a LED light, infrared light, a UV light, a laser light, photo reactive chemical producing light, phosphorus or any other suitable light source generating the light in a range of 100-1600 nm wavelength for treating a person.

The light direction controller 112 follows a treatment portion of a user body to an extent by changing a direction of the light projection. Further, once the treatment portion starts moving out of reach of the light direction controller 112 the rotation head 250 that rotates on the spindle 230 with the help of a motor keeps the light projection intact on the treatment portion of the user body regardless of the movement of the user body or the treatment portion.

Further, the camera unit 120 is having a camera 121 and at least one sensor 122. Wherein, the camera 121 is selected from a group of a normal optical camera, a thermographic camera, an infrared spectroscopy camera, an IP camera and a combination thereof. Further, the at least one sensor is selected from group of non-contact type sensors including radiation detectors, optical pyrometers, fiber optic temperature sensors, IR sensors, temperature sensors, thermal imaging sensor, ultrasonic, and infrared sensors etc.

According to an embodiment of the present disclosure, the power unit 170 is having a rechargeable battery and a port for charging the battery via, a USB cable or a power adapter etc. Further, the power unit 170 is mounted in the second housing 220 in a way that it is electrically connected to the rotation unit 150, the camera unit 120, the controlling unit 130, the memory unit 140 and the light projection unit 110.

The light projection unit 110 project a light of a 100-1600 nm wavelength which is suitable for various skin and/or body condition treatments. Further, the light head 111 keeps the projected light away from the user's eyes, as the certain wavelength of the light projection could be hazardous to the human eyes.

The controlling unit 130 uses an artificial intelligence module, machine learning module, localization module, object detection module and image processing module in order to automatically identify, select, localize and prioritize the at least one body condition. Further, the controlling unit also utilizes the artificial intelligence module, machine learning module, localization module, object detection module and image processing module to automatically selecting a treatment based on the body condition of the user and automatically projecting a light based on the body condition without or with minimum user intervention.

Localization Module: the localization module provides a complete visual module to localize objects using the camera. The localization module requires a preprocessing algorithm to segment a scene into objects. Ideally, the preprocessing algorithm should be able to segment an unstructured scene into objects using visual cues such as shape, texture, edges, and color in real-time. In the lack of a preprocessing algorithm which can satisfy all these constraints for a completely unstructured environment, one is forced to put some structure into the environment to make the detection and segmentation of objects easier.

Object detection Module: The Object detection module provides a way to identify specifically trained objects within the current image. Once the module is trained with sample template images it will identify those objects within the current image depending on the filtered parameters of confidence, size, rotation, etc.

Artificial intelligence and machine learning module: the controlling unit utilizes artificial intelligence and machine learning modules to estimate a predictive model that best generalizes to a particular type of data. Therefore, for solving a problem by machine learning and artificial intelligence, it is imperative to have a large number of examples that can be used by the learning algorithm to understand the system's behavior and similar kind of predictions can be generated by the light therapy device when the machine learning algorithm is presented with new examples of data. According to present disclosure, the system records and learn various methods of treatment used by the user for different or body conditions. E.g. if a user uses UV light of a particular intensity and shape for a predefined time period on a particular body disorder the light therapy device uses artificial intelligence and machine learning module to learn and record all the events happened during the treatment and in future if the light therapy device is presented with similar skin disorder or body problem it uses its learning from the previous similar treatment and can automatically provide treatment based on the learning.

Figure 3:
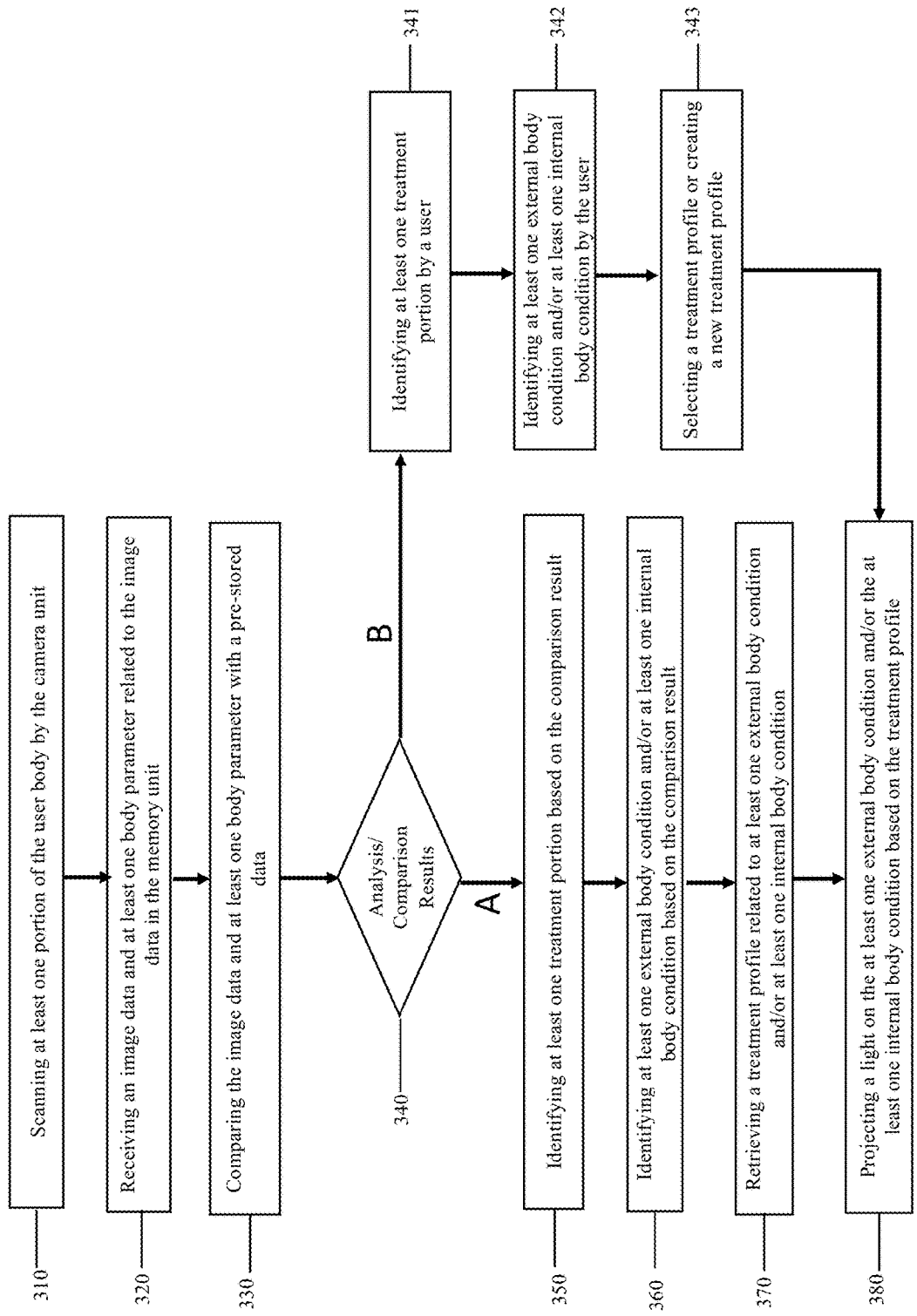
FIG. 3 Shows a flowchart of light therapy process according to an embodiment of the present disclosure.

Referring to FIG. 3, shows a flowchart of the light therapy process 300 according to an embodiment of the present disclosure, a user switches on the light therapy device 200 by using a power button (not shown) mounted on an outer surface of the light therapy device 200 and puts at least one portion of the user body in front of the camera unit 120. The camera unit 120 starts scanning the at least one portion of the user body, at step 310, the at least one portion of the user body includes a face, hand, head, leg, chest, stomach, genital area etc. or full body of the user. The camera unit 120 having the camera 121 is adapted to capture an image data of the at least one portion of the user body and the at least one sensor 122 of the camera unit 120 is collecting at least one body parameter related to the image data, the at least one body parameter includes heart rate, blood flow, temperature and other parameters related to image data. In step 320, the memory unit 140 receives the image data and the at least one body parameter related to the image data.

Further, at step 330 the controlling unit 130 by using object detection module, artificial intelligence module, localization module, machine learning module and image processing module compares and analyzes the image data and the at least one body parameter related to the image data with a pre-stored data stored in a database of the memory unit 140, further an analysis and comparison results are displayed via the display unit 160 in step 340.

According to situation A, if at step 340, the image data and the at least one body parameter related to the image data matches completely with the pre-stored data stored in the databased of the memory unit 140. The controlling unit 130 by using an artificial intelligence module and machine learning module automatically identifies at least one treatment portion from the image data based on the comparison results at step 350. Wherein, the at least one treatment portion of the user body includes a face, hand, head, leg, chest, stomach, genital area etc. or full body of the user that needs to be treated. Further, at step 360 the controlling unit 130 identifies at least one external body condition and/or at least one internal body condition from the at least one treatment portion based on the analysis and comparison results.

Wherein, the at least one external body condition includes skin disorder, skin problems, skin cancer, aged skin, dead skin, sun tanning, wounds, allergy, inflammation, dermatitis, hives, marks, acne, redness, irritants, itching, swelling, sebaceous, lesions pimples, wrinkles or combination thereof and the at least one internal body condition includes a blood flow, fever, erectile dysfunction, joints pain, muscles pain, grey hair, hair fall, eyebrows, cellular improvement, sleep disorder, jaundice, cancer, internal body problems, and combination thereof.

Further, at step 370, the controlling unit 130 retrieves a treatment profile from the memory unit 140 related to at least one external body condition and/or at least one internal body condition. Wherein, the treatment profile includes the information related to temperature, blood flow, heart rate, external body condition, internal body condition, type of light therapy, intensity of a light, shape of light projection and any other information required for providing light therapy to the at least one external body condition and/or at least one internal body condition.

Furthermore, at step 380, the controlling unit 130 allows the light projection unit 110 to project a light on the at least one external body condition and/or the at least one internal body condition according to the treatment profile.

According to situation B, if at step 340, the image data and the at least one body parameter related to the image data partially matches or do not matches with the pre-stored data of the database, the controlling unit 130 allows the user to manually identify at least one treatment portion from the image data at step 341. Further, at step 342, the controlling unit 130 allows the user to manually identify at least one external body condition and/or at least one internal body condition via the display unit 160. Furthermore, the controlling unit 130 allows the user to select a treatment profile from the memory unit 140 or to create a new treatment profile based on his/her own intellect or other references e.g. internet, books, literature etc. via the display unit 160 at step 343. After selecting or creating the treatment profile at step 343, the controlling unit 130 allows the light projection unit 110 to project a light on the at least one external body condition and/or the at least one internal body condition based on the treatment profile at step 380.

Figure 2:
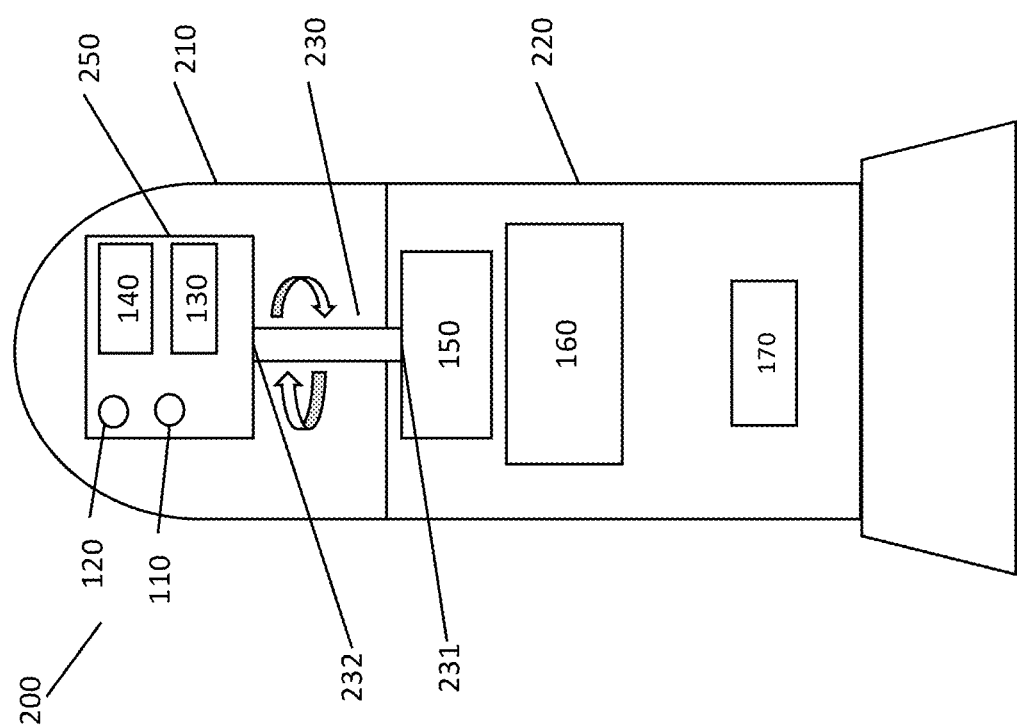
FIG. 2 Shows the light therapy device according to an embodiment of the present disclosure.
Figure 4A:
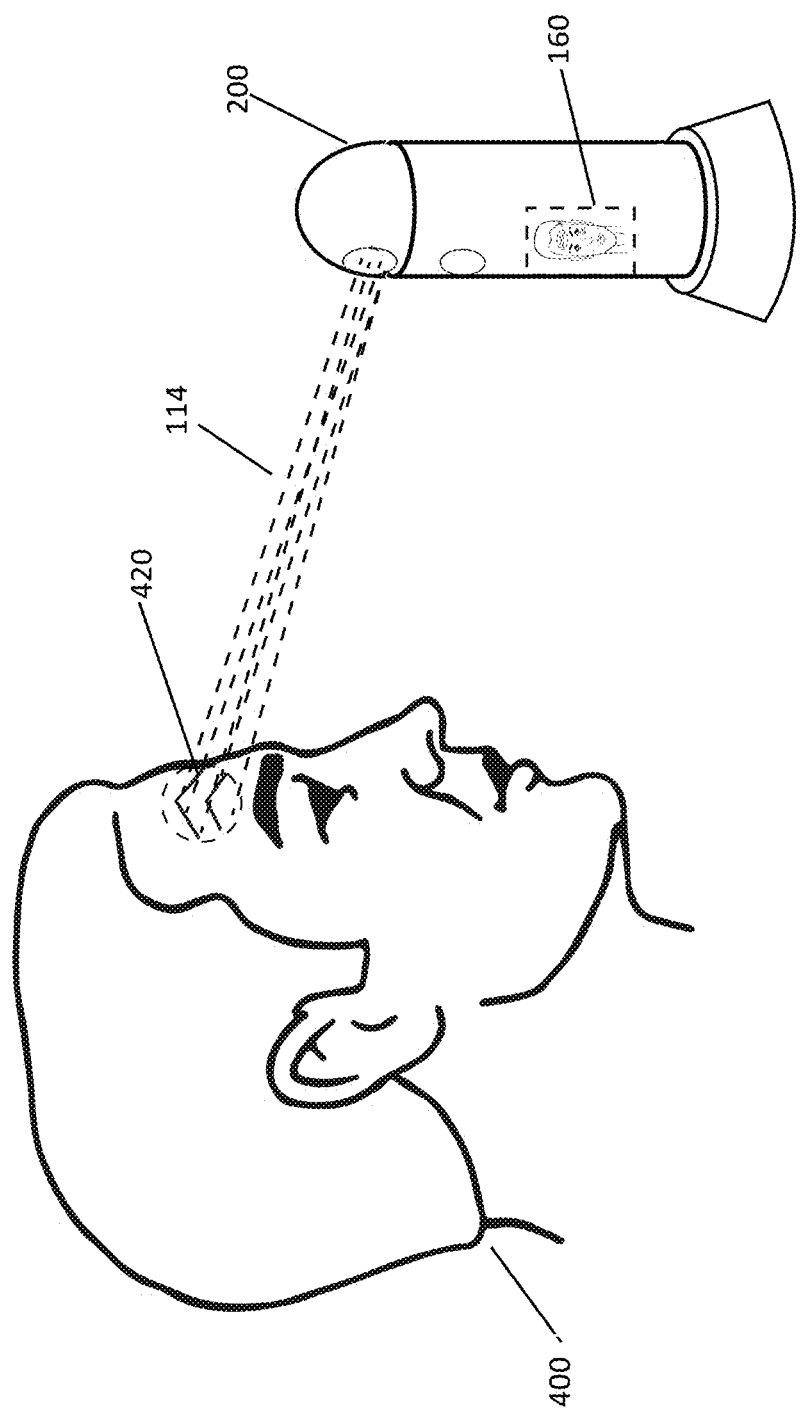
FIGS. 4A and 4B are showing a configuration of the light therapy device according to an exemplary embodiment of the FIG. 2.
Figure 4B:
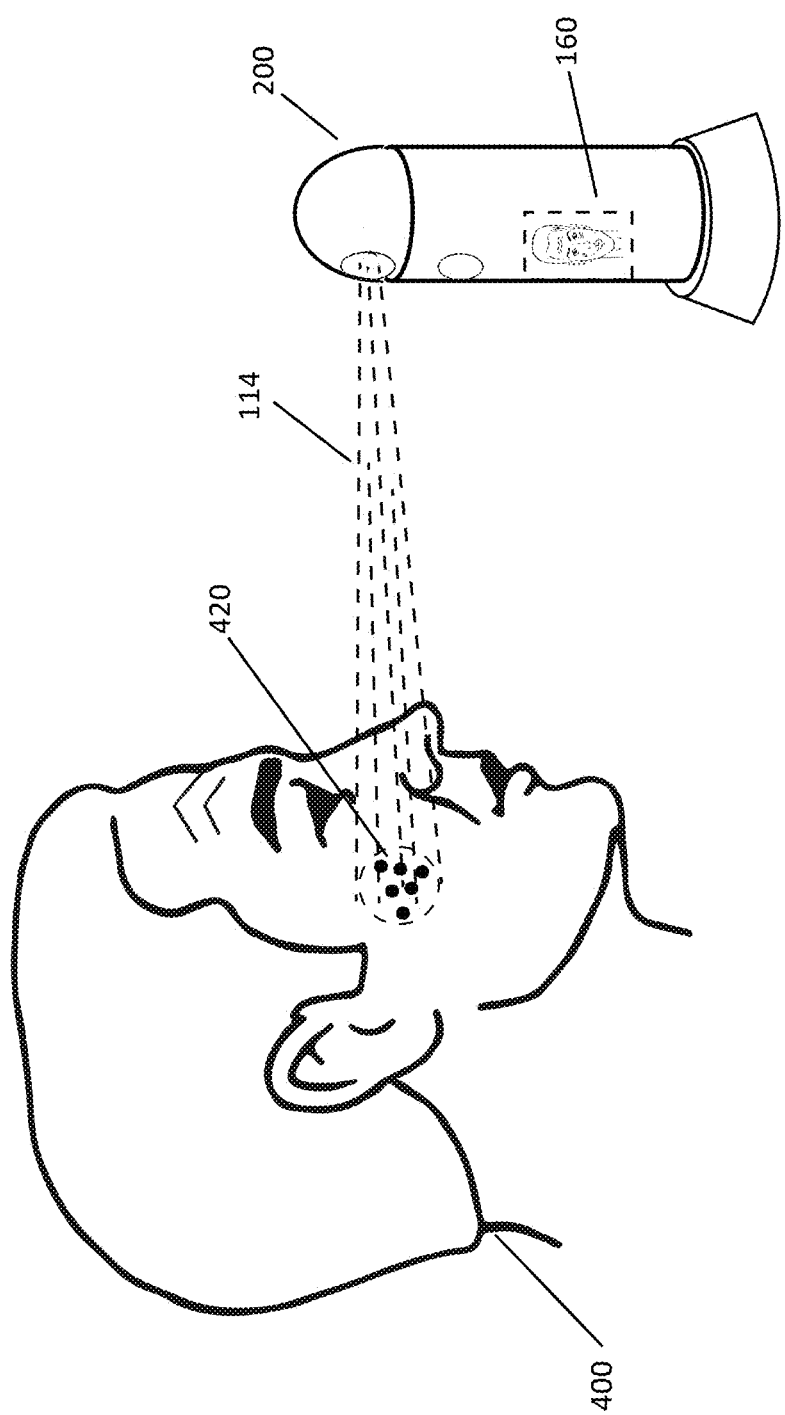

Referring to FIGS. 4A and 4B, a user 400 using the light therapy device 200 according to an exemplary embodiment of the FIG. 2. In FIG. 4A, the light therapy device 200 identifies a treatment portion 420 on a forehead area of the user 400 automatically by using an artificial intelligence module, the machine learning module, the object detection module, the localization module and the image processing module or the user 400 manually selects the treatment portion 420 via the display unit 160 and projecting a light 114 on the treatment portion 420.

Further, in FIG. 4B, the light therapy device 200 identifies a treatment portion 420 on a cheek area of the user 400 automatically by using the artificial intelligence module, the machine learning module, the object detection module, the localization module and the image processing module or the user 400 manually selects the treatment portion 420 via the display unit 160 and projects a light 114 on the treatment portion 420.

According to yet another embodiment of the present disclosure, the image data is the real-time data, in which the camera 121 captures the live image or video data of the treatment portion of the user body According to yet another embodiment of the present disclosure, the controlling unit is able to create a separate user profile for each user where the user can store his/her previous treatment record, treatment profiles, user details, image data, video data etc.

According to yet another embodiment of the present disclosure, the sensors used for detecting the movement of the treatment portion of the user body could be Passive Infrared (PIR) Sensors, Ultrasonic Sensors, Microwave Sensors or any other suitable sensors that can be used for motion detection.

According to yet another embodiment of the present disclosure, the light therapy device 200 uses a low wavelength light that can heal the areas near a user's eyes.

According to yet another embodiment of the present disclosure, the light therapy device 200 can work without having a display unit 160. In this, the user places at least one treatment portion in front of the light therapy device 200 and the light therapy device 200 automatically scan, identify, select, prioritize and treat the at least one treatment portion with the help of the artificial intelligence, machine learning, object detection, image processing module and the localization module.

According to yet another embodiment of the present disclosure, the light therapy device is having a calibration protocol to identify the 3D co-ordinates (X, Y, and Z) of the portion of the user body to be treated. Further, the calibration protocol uses a 3D (3-dimensional) object detection method to extract the 3D co-ordinates (X, Y, and Z) of the treatment portion. Based upon the 3D co-ordinates the light direction controller 112 projects the light 114 on the treatment portion and follows the motion of the treatment portion of the user to a predefined distance.

According to yet another embodiment of the present disclosure, the mirror galvanometer (not shown) acts as the light direction controller 112. A light from the light source 113 is made to fall on at least one mirror of the galvanometer and the controlling unit provides input to the galvanometer, based on the controlling unit 130 input the coil of the galvanometer rotates and projects the light in the desired direction through the light head 111. In this, the galvanometer consists of at least one coil which is suspended by means of silken threads. At least one mirror is attached to the at least one coil. The light from the light source is made to fall on the mirror. The reflected light will fall on a light head attached to the mirror galvanometer. When the coil deflects the mirror deflects with it. The light which is deflected also moves on a treatment portion of the user body. The distance on the treatment portion determines the sensitivity of the galvanometer.

According to yet another embodiment of the present disclosure, the light therapy device 200 is using the artificial intelligence machine learning object detection and the localization modules in order to control the ON/OFF operations of the light therapy device 200. In this, the light therapy device 200 will automatically shut OFF when the treatment portion of the user is out of a predefined distance. The light therapy device 200 automatically switches ON when the user again enters in the predefined distance range of the light projection. Further, the light therapy device 200 may automatically shut ON/OFF with the help of head movement or hand gesture of the user.

The light therapy device 200 does not select the area near the user's eyes for the treatment as it can be hazardous to the eyes, the light therapy device 200 uses low wavelength light projection for treating the area near the user's eye. Further, the controlling unit 130 does not allow the light projection to go beyond the treatment portion or a predefined distance.

According to yet another embodiment of the present disclosure, the display unit 160 is a touchscreen display mounted on the outer surface of the light therapy device acting as an input unit, in which the user can manually select and prioritize the external body condition and/or the internal body condition based upon his/her own intellect. Further, the user can determine the type of treatment required for a particular body condition and can also determine the time and intensity required for the treatment.

According to yet another embodiment of the present disclosure, a remote device connected to the light therapy device 200 via a wired or wireless (NFC, Wi-Fi, Bluetooth) communication means, which is configured to display the image data from the camera unit. Further, the remote device allows the user to manually identify, select, and prioritize the at least one body condition, and the user is allowed to select a treatment based on the body condition and provide input to the light projection unit based upon his own intellect. Further, the user can select the intensity, shape, time period of the light projection as per the body condition. Wherein, the remote device is a mobile, laptop, remote control or any other device allows the user to provide inputs.

The light therapy device 200 is also used by a professional (a physician, a dermatologist, a lab technician, a beautician etc.) to provide therapy to others. In this, the professionals can remotely monitor and provide inputs to the patient through the remote device. Further, the light therapy device can be used by the normal person and can be used for treating animals as well.

Figure 5:
FIG. 5 Shows the light therapy device with a mobile device according to a second embodiment of the present disclosure.

Referring to FIG. 5, the light therapy system 100 comprises of a remote device i.e. a mobile device 520 held by a user and a light therapy device 200 according to a second embodiment of the present disclosure. The mobile device 520 is communicatively coupled to the light therapy device 200 via NFC, WI-FI, Bluetooth or any other wired or wireless communication means. The display of the mobile device 520 acts as a display unit 160 for the light therapy device 200. The mobile device 520 is having a software application installed in it. The software application provides a user interface 430 where a user can find multiple options to select in order to communicate with the light therapy device 200. Once the mobile device is connected with the light therapy device 200 the user is able to control the light therapy device 200 via the user interface. The user 400 is able to see his/her portion of the body that needs to be treated on the mobile device 520 display and is able to adjust the portion of the body that needs to be treated according to best view.

Figure 6:
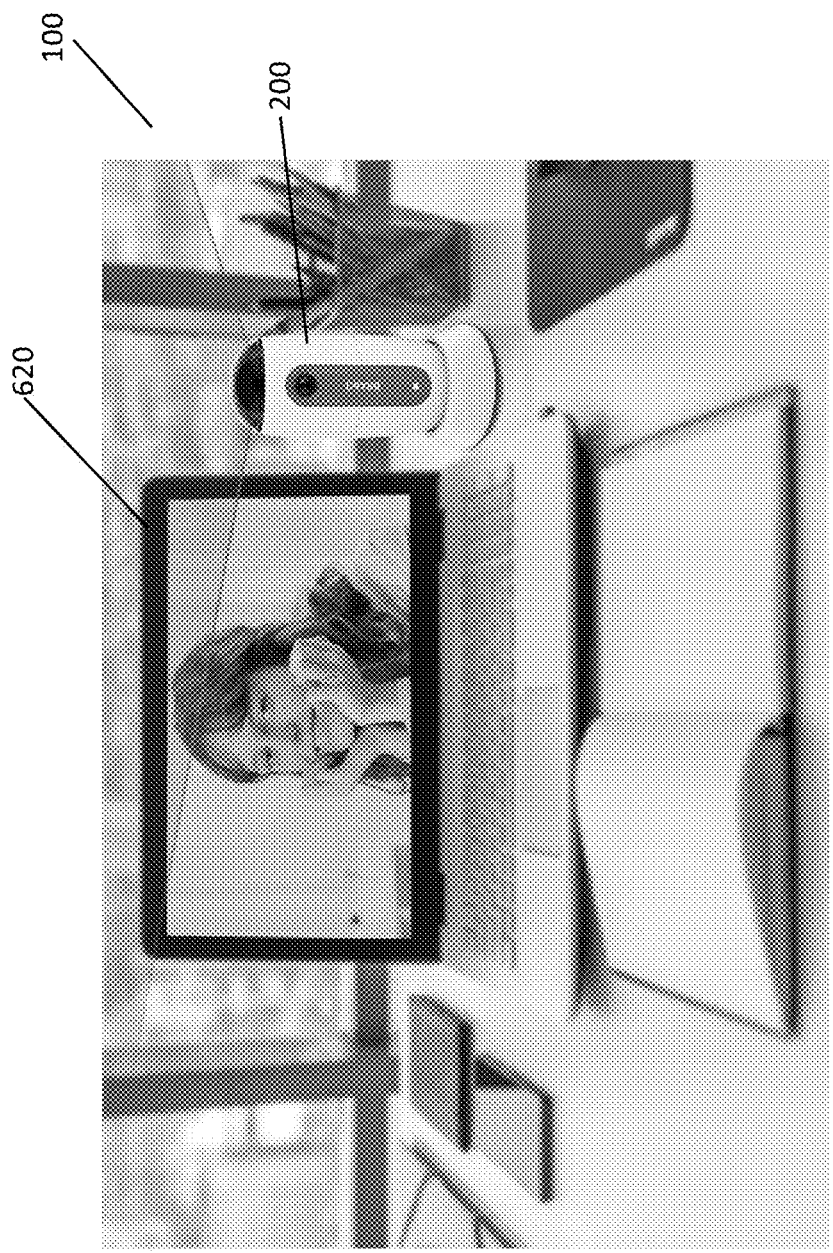
FIG. 6 Shows the light therapy device with a laptop according to a third embodiment of the present disclosure.

Referring to FIG. 6, according to a third embodiment of the present disclosure, the light therapy system 100 in which a user wirelessly connects the remote device i.e. a laptop 620 with the light therapy device 200 and the image data from the camera unit 120 displays on the laptop display where the user can manually select and prioritize the body conditions based upon his/her own intellect. Further, the user can determine the type of treatment required for a particular body disorder and can also determine the time and intensity required for the treatment.

Figure 7:
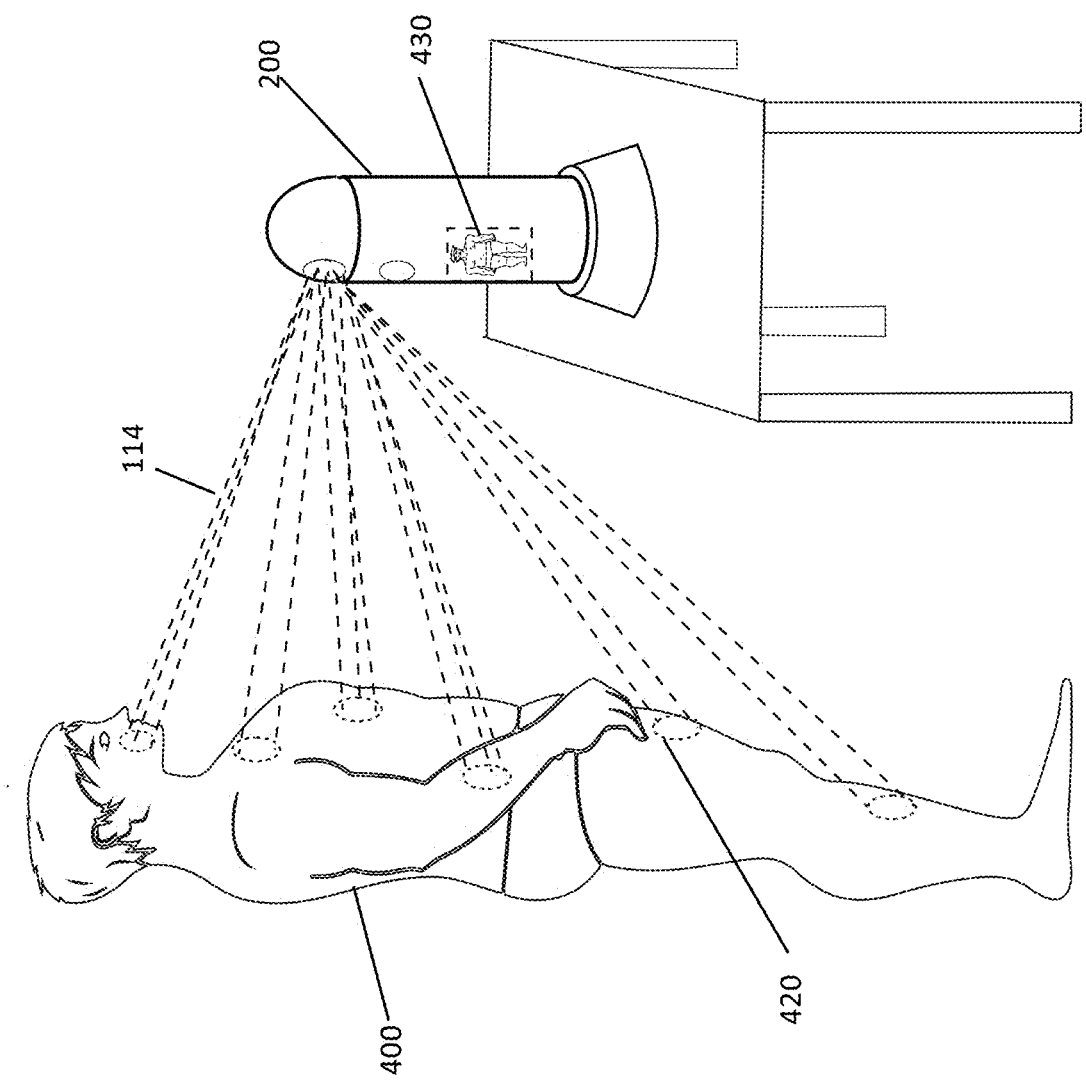
FIG. 7 Shows a configuration of the light therapy device according to an exemplary embodiment of the FIG. 2.

Referring to FIG. 7, the light therapy device 200 is used for providing multiple body parts treatment in one time according to an exemplary embodiment of the FIG. 2, wherein a user 400 is standing in front of the light therapy device 200 and the camera 121 is scanning and identifying the body conditions on the user 400 body. Further, the user interface 430 is showing the image data on the display where the user can manually or the device can automatically identify, select, prioritize and treat the body conditions by using artificial intelligence, machine learning, localization module, image processing module, and object detection module.

Figure 8:
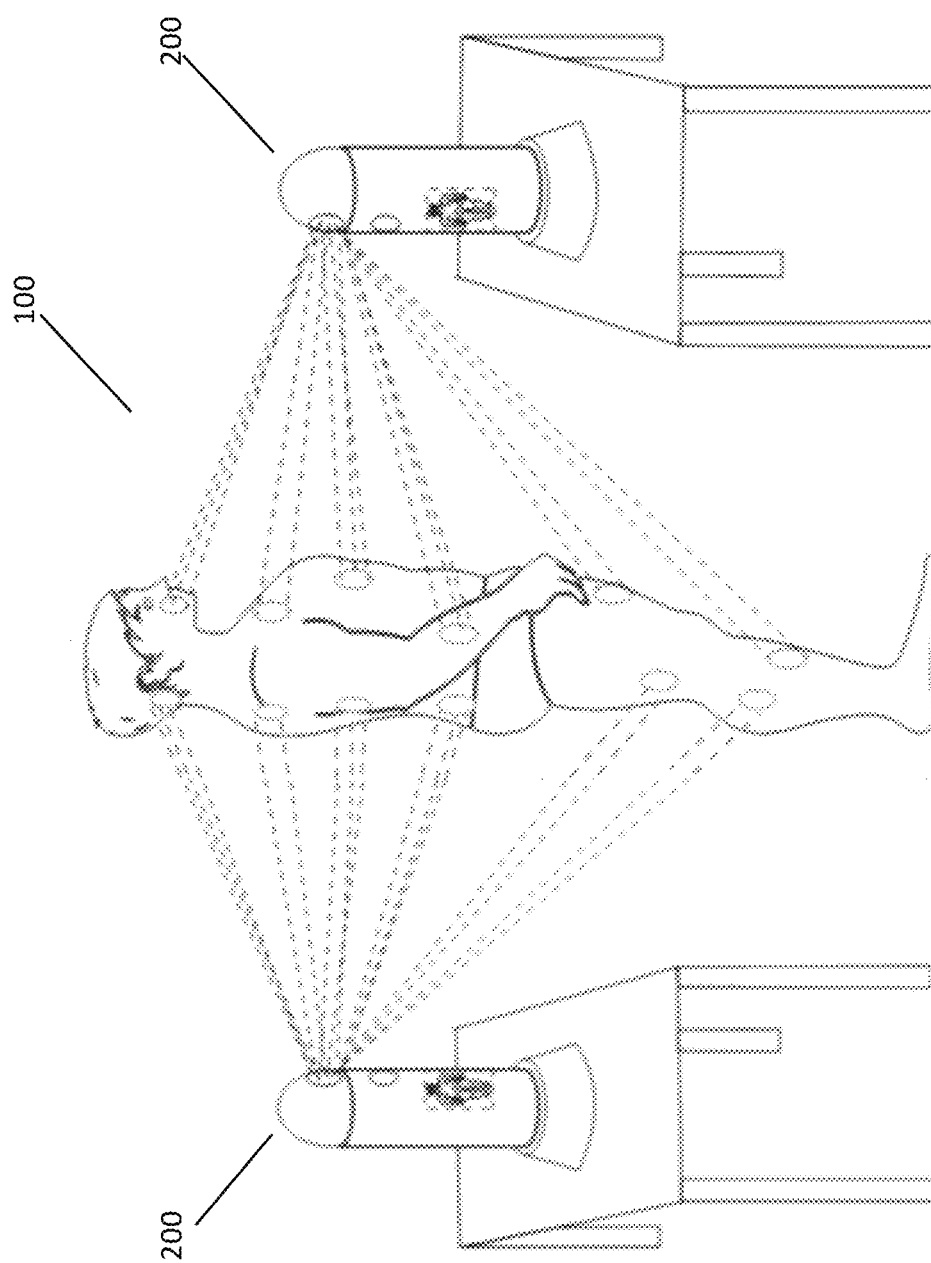
FIG. 8 Shows a user using two light therapy devices according to an exemplary embodiment of the FIG. 2.

Referring to FIG. 8, the light therapy system 100 is having two light therapy device 200 according to an exemplary embodiment of the FIG. 2, the first light therapy device 200 is placed towards the front side of the user and the second light therapy device 200 is placed towards the backside of the user. To use, the user activates the first and second light therapy device by turning ON the power button or by a head movement or by a hand gesture. The first and second device establish a connection through wired or wireless means with each other in order to work in synchronization. The first and the second devices start scanning the corresponding body portions of the user body and each identifies the at least one treatment portion. Here, first and second light therapy devices have separate treatment portions. Further, the first and second light therapy devices identify the at least one body condition from their respective treatment portions. Further, the first and second light therapy device projects the light on their respective treatment portions. The first and the second light therapy devices are identical to each other and are being used together to cover the maximum body portion of the user at one time.

Further, the first and second light therapy device may connect to the remote display device and a user can manually select, identify, and prioritize the skin disorder based upon his/her knowledge or intellect.

Figure 9:
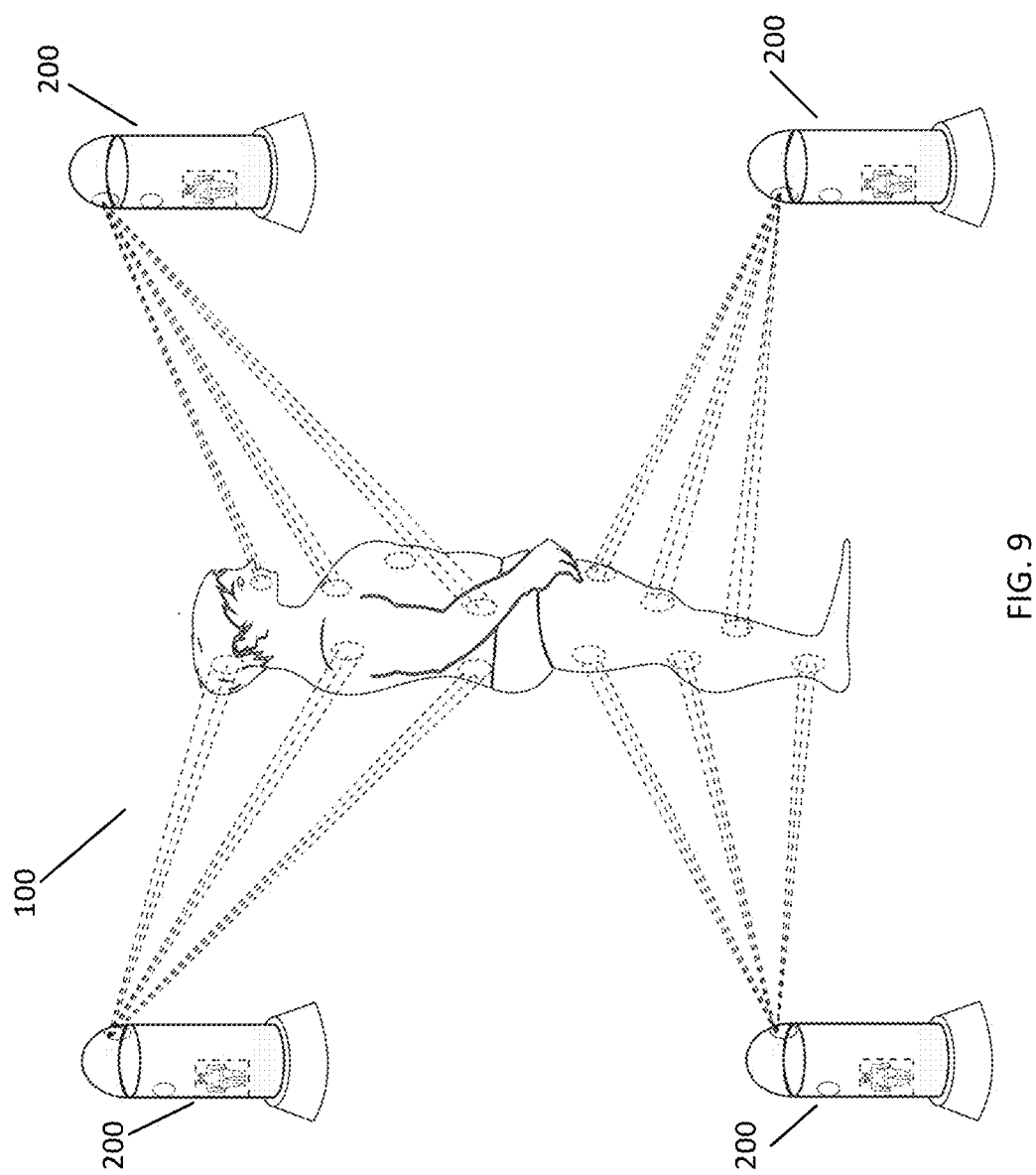
FIG. 9 Shows a user using a plurality of light therapy devices according to an exemplary embodiment of the FIG. 2.

Referring to FIG. 9, show a light therapy system 100 according to an exemplary embodiment of the FIG. 2, wherein a user is using a plurality of light therapy devices 200 for full body treatment at a time. In this, the user is surrounded by the plurality of light therapy devices and each light therapy device is projecting light towards a separate treatment portion on the user body.

According to yet another embodiment of the present disclosure, the light therapy system uses a master-slave model. Further, the two or more light therapy devices are used in which one light therapy device acts as a master light therapy device and the rest of the light therapy devices acts as a slave to the master light therapy device. All the light therapy devices including master light therapy device and slave light therapy devices are linked with each other and forming a peer to peer network. In this, the master light therapy device has a controlling unit which is controlling the all other slave light therapy devices, each of the slave light therapy devices is having a communication module to communicate with the master light therapy device and a light projection unit works as per the master light therapy device input. To use this, the user activates the master light therapy device and the master light therapy device establishes a wired or wireless connection with other slave light therapy devices, the master device identifies the location and position of the user and allocates separate treatment portion to each slave light therapy device by using artificial intelligence, machine learning, object detection and localization module or the user may manually select, identify, locate and treat the separate treatment portion for each light therapy device Peer to Peer network: Peer-to-peer (P2P) computing or networking is a distributed application architecture that partitions tasks or workloads between peers. Peers are equally privileged, equipotent participants in the application. They are said to form a peer-to-peer network of nodes. Peers make a portion of their resources, such as processing power, disk storage or network bandwidth, directly available to other network participants, without the need for central coordination by servers or stable hosts. Peers are both suppliers and consumers of resources, in contrast to the traditional client-server model in which the consumption and supply of resources are divided. Emerging collaborative P2P systems are going beyond the era of peers doing similar things while sharing resources, and are looking for diverse peers that can bring in unique resources and capabilities to a virtual community thereby empowering it to engage in greater tasks beyond those that can be accomplished by individual peers, yet that are beneficial to all the peers.

Master-slave model: Master/slave is a model of communication where one device or process has unidirectional control over one or more devices. In some systems, a master is elected from a group of eligible devices, with the other devices acting in the role of slaves.

According to yet another embodiment of the present disclosure, the light therapy device 200 generates and provides a treatment report regarding the improvement after the diagnosis or treatment of the body condition. In addition, the report displays the information of the percentage of improvement in the particular body condition after the treatment or diagnosis e.g. the particular acne has been 0.005 percentage reduced since last treatment or diagnosis.

According to yet another embodiment of the present disclosure, the light source 113 projecting the light on the light direction controller 112 is selected from a group of LED light, a laser light, an Infrared light, UV Light, an electromagnetic light or any other suitable light that helps in body treatment.

According to yet another embodiment of the present disclosure, the remote device could be a mobile phone device, a computer, a laptop or any other suitable device that is able to connect with the light therapy device 200 via wired or wireless (NFC, WI-FI, Bluetooth etc.) connection means. The remote device is having a display where the user can see the scanned or image data from the camera unit and have an input means to provide user input. Further, the remote device may be a device that provides remote access to a doctor, a dermatologist, a clinician or any other health counsel so that the user can be remotely analyzed and guided by the professionals.

According to yet another embodiment of the present disclosure, the light therapy device can make audible alerts every time a new treatment session starts or completes.

According to an advantageous embodiment of the present disclosure, the light therapy device provides Photodynamic Therapy (PDT) or Photo-chemotherapy. In this, a chemical substance is activated by the light, used in conjunction with molecular oxygen to elicit cell death. PDT has the ability to kill microbial cells, including bacteria, fungi and viruses and treating acne. It is used clinically to treat a wide range of medical disorders, including wet age-related macular degeneration, psoriasis, atherosclerosis and has shown some efficacy in anti-viral treatments, including herpes. Further, the PDT also helps in treating malignant cancers including head and neck, lung, bladder, and particular skin. PDT is both minimally invasive and minimally toxic. Furthermore, the PDT applications involve three components: a photosensitizer, a light source, and tissue oxygen. The wavelength of the light source needs to be appropriate for exciting the photosensitizer to produce radicals and/or reactive oxygen species. These are free radicals (Type I) generated through electron abstraction or transfer from a substrate molecule and highly reactive state of oxygen known as singlet oxygen (Type II). PDT is a multi-stage process. First, a photosensitizer with negligible dark toxicity is administered, either systemically or topically, in the absence of light. When a sufficient amount of photosensitizer appears in diseased tissue, the photosensitizer is activated by exposure to light for a specified period. The light dose supplies sufficient energy to stimulate the photosensitizer, but not enough to damage neighboring healthy tissue. The reactive oxygen kills the target cells.

According to an advantageous embodiment of the present disclosure, the device provides intense pulsed light (IPL) treatment. In this, a high-powered, computer-controlled, visible, broad-spectrum pulse of light, generally in the visible spectral range of 400 to 1200 nm and a frequency range of 1 to 1,000,000 (Hz) with or without variable hertz is delivered. Various cutoff filters are commonly used to selectively filter out shorter wavelengths, especially potentially damaging ultraviolet light. The resulting light has a spectral range that targets specific structures and chromophores (e.g. melanin in hair, or oxyhemoglobin in blood vessels) that are heated to destruction and reabsorbed by the body. IPL shares some similarities with laser treatments, in that they both use light to heat and destroy their targets. But unlike lasers that use a single wavelength (color) of light which typically matches only one chromophore, and hence only one disorder, IPL uses a broad spectrum that when used with filters, allows it to be used against several disorders. IPL can provide various skin treatments for aesthetic and therapeutic purposes, including hair removal, photo rejuvenation (e.g. the treatment of skin pigmentation, sun damage, and thread veins) as well as to alleviate dermatologic diseases such as acne, marks etc.

According to an advantageous embodiment of the present disclosure, the light therapy device analyzes a refractive index of a treatment portion of the user body and provides treatment based on the refractive index of the treatment portion. Further, the light therapy device adjusts focus of the light projection in case the light rays scattering out of the treatment portion (towards sensitive areas e.g. eyes) and making user uncomfortable, the light therapy device by analyzing the refractive index of the sensitive areas adjusts the focus of the light and attenuates the light rays to go beyond the treatment portion.

According to an advantageous embodiment of the present disclosure, the light therapy device is using a specific wavelength of light for treating neonatal jaundice. Neonatal jaundice is a yellowish discoloration of the white part of the eyes and skin in a newborn baby due to high bilirubin levels.

According to an advantageous embodiment of the present disclosure, the light therapy device also uses a specific wavelength of light to treat a port-wine stain (nevus flammeus), commonly called a firemark. The port-wine stain is a discoloration of the human skin caused by a vascular anomaly (a capillary malformation in the skin).

According to an advantageous embodiment of the present disclosure, the light therapy device uses seven frequencies which were developed by Dr. Paul NOGIER in the 1970s. These frequencies are constantly used in routine medical practice, as they are preferentially recognized by the body. They enter into resonance with the body and exert specific effects on the body. These frequencies are used both for detection and for treatment. The same frequencies are used for laser devices, but at a higher harmonic.

Definition of frequencies by Dr. Paul and Raphael NOGIER:
A: action on the tissues wounds, epithelial tumors, epidermal reactions;
B: gastrointestinal and metabolic problem strophic functions, polarity, parasympathetic, interceptive impulses;
C: locomotor problems, Ergo tropic function, sympathetic polarity;
D: disorders of laterality;
E: pain and nerve conduction spinal cord diseases;
F: brain and bone reconstruction;
G: action on the cerebral cortex cortical, mental disorders;
The effects can be potentiated by associating various frequencies. These combinations of frequencies are especially used in local therapy:
E.g. For Analgesic, frequencies E and G; For Regenerating, frequencies A, B, and F; For Muscle Relaxing, frequencies C, D and G
A user can choose the individual configuration and use with all available power, wavelengths, frequencies, and functions. In this, the user can simply choose frequencies corresponding to body part and pathology.
A. Body openings, tonification, acute diseases, inflammation;
B. Abdomen, sedation, chronic diseases, metabolism;
C. Muscles, bones, joints, circulation, movement disorders;

D. Commissural, brain frequencies, stress balance, relaxation;
E. Nerves, pain, neuralgia, herpes zoster, spinal cord;
F. Face, mouth, brain frequency, psychic/psychosomatic symptoms;
G. Frontal brain, intellectual disorder, anxiety, muscle strain.

According to an advantageous embodiment of the present disclosure, the light therapy device uses a thermographic camera. the thermographic camera forms an image using infrared radiation, similar to a common camera that forms an image using visible light. Instead of the 400-700-nanometer range of the visible light camera, infrared cameras operate in wavelengths as long as 1600 nm. A special lens focuses the infrared light emitted by all of the objects in view. The focused light is scanned by a phased array of infrared-detector elements. The detector elements create a very detailed temperature pattern called a Thermogram. Thermal imaging cameras take measuring temperature to the next level, instead of getting a number for the temperature it shows a picture displaying the temperature differences of a surface.

Further, the thermographic camera can easily identify the portions of the user body having different body temperature. This will allow the light therapy device to identify the areas with increased blood flow (Generally the areas with increased blood are mostly inflammations) and the light therapy device is able to provide treatment based on the blood flow or temperature of the body portion. The use of thermographic camera further allows the light therapy device to identify the areas which do not have sufficient blood flow the light therapy device by using the infrared or red light improves the rate of blood flow in these areas. Further, based on the temperature of different portions of the body the light therapy device can analyze the various body disorder easily and can provide treatment according to the body condition or disorder.

According to an advantageous embodiment of the present disclosure, the light therapy device provides Low-level Laser Therapy (LLLT). LLLT is a non-invasive light source treatment that generates a single wavelength of light. It emits no heat, sound, or vibration. It is also called photobiology or bio stimulation or Photo-bio-modulation Therapy (PBMT). LLLT affects the function of connective tissue cells (fibroblasts), accelerate connective tissue repair and act as an anti-inflammatory agent. Lasers with different wavelengths, varying from 632 to 904 nm, are used in the treatment of musculoskeletal disorders. Further, the wavelengths between 660 nm and 905 nm have the ability to penetrate the skin and soft/hard tissues. This light has a good effect on pain, inflammation and tissue repair.

According to an advantageous embodiment of the present disclosure, the light therapy device can be used for treating erectile dysfunction by illuminating the light on the genital area of the user. The light source is sufficient to induce relaxation of the walls of the blood vessels supplying blood to the corpora cavernosum of the penis. Further, the light source in a quantity and over a surface area of the penis provides sufficient stimulation to improve the male's ability to achieve and maintain penile erection. In addition, the light therapy device emits a light energy, preferably at a wavelength of 1072 nanometers, is applied to the genitalia area of male, female humans and animals to treat erectile dysfunction (ED). The light causes the release of nitric oxide into the erectile genitalia tissue, and the nitric oxide causes the smooth erectile tissue to relax and engorge, thereby facilitating erection.

According to an advantageous embodiment of the present disclosure, the light therapy device could provide different types of treatment based on the body condition e.g., laser light-based treatment, LED (light emitting diode), Photodynamic therapy (PDT), Photo-bio-modulation therapy, UV based therapy and any other suitable therapy required for particular body disorder.

According to an advantageous embodiment of the present disclosure, the device could provide various body treatments e.g. Increasing blood flow, cellular repair, tissue repair, muscle repair, bone repair, wound healing, skin disorders (acne, marks, hives, pimples, herpes, redness, inflammation, itching, irritant, infection, cutaneous disorder, rosacea and any other dermatological problem or disorder) improvement, erectile dysfunction, hair treatment, eyebrow treatment, nose allergy temporomandibular joint dysfunction (TMJ), oral mucositis etc. by using Photo-bio-modulation Therapy, Photodynamic Therapy, UV based light therapy or any other suitable light based therapy.

According to an advantageous embodiment of the present disclosure, the light therapy device provides a LED light-based treatment which is a painless, relaxing, non-invasive skin-care treatment that has multiple benefits particularly stimulating collagen and require no downtime. Further, LED treatments work by using an array of bright light-emitting diodes that send low-level light energy into the deeper layers of the skin.

According to an advantageous embodiment of the present disclosure, the light therapy device uses infrared light which tends to be used to treat wrinkles and other problems caused by poor skin support, such as translucent skin or coarse skin.

According to an advantageous embodiment of the present disclosure, the light therapy device uses laser treatment for diagnosing TMJ (Temporomandibular Joint Dysfunction) In this, the light photons (energy) penetrates deep into the tissues surrounding the temporomandibular joint as well as the joint itself. Laser energy decreases inflammation deep in the tissues that produce almost immediate relief. It also stimulates healing.

According to an advantageous embodiment of the present disclosure, the light therapy device uses infrared light to treat hay fever and other allergic rhinitis symptoms such as a runny nose, itching, and sneezing. The devices emit infrared light with a specific wavelength into the nasal cavity, which makes the nasal mucous membranes less sensitive to triggers such as pollen of flowering plants and trees or other allergens.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Although specific embodiments and certain structural arrangements have been illustrated and described herein, it will be clear to those skilled in the art that various other modifications and embodiments may be made incorporating the spirit and scope of the underlying inventive concepts and that the same is not limited to the particular methods and structure herein shown and described except in so far as determined by the scope of the appended claims.

NAME OF THE COMPONENT AND REFERENCE NUMERAL light therapy System 100
Light Projection Unit 110
Light Head 111
Light Direction Controller 112
Light Source 113
Projected Light 114
Camera Unit 120
Camera 121
Sensor 122
Controlling Unit 130
Processor 131
Memory Unit 140
Rotation Unit 150
Display Unit 160
Power Unit 170
Light Therapy Device 200
First Housing 210
Second Housing 220
Rotatable Head 250
Spindle 230
First End of the Spindle 231
Second End of the Spindle 232
User 400
Desired treatment Portion 420
Mobile device 520
Laptop 620
User Interface 430

What is claimed is:

1. A device for providing light therapy to a user body, the device comprising:
a rotatable head including a light projection unit, a camera unit, and a memory unit operably connected with a controlling unit;
a first housing including a spindle adapted to rotate, wherein the rotatable head has been included in the first housing and mounted onto the spindle;
a second housing including a rotation unit, wherein the rotation unit includes a motor; and
wherein the first housing is mounted on the second housing;
wherein a first end of the spindle is connected with the motor and a second end of the spindle is connected with the rotatable head;
wherein the camera unit includes a camera and at least one sensor, wherein the memory unit includes a database having pre-stored data, wherein the pre-stored data is related to a plurality skin conditions, a plurality of internal body conditions, a plurality of treatment profiles corresponding to the plurality of skin and internal body conditions, and a plurality of user profiles corresponding to a plurality of respective users;
wherein the controlling unit is operably connected to the camera unit, the memory unit, and the light projection unit, and
wherein the controlling unit includes a processor adapted to execute a computer implemented code stored in the memory unit, in order to control functionalities of the camera unit, the memory unit, and the light projection unit, the computer implemented code when executed by the processor, enables the processor to perform following steps of:
scanning the user body, by the camera unit, to capture image data and at least one body parameter of the user body, wherein the camera is adapted to capture the image data and the at least one sensor is adapted to collect the at least one body parameter,
storing the image data and the at least one body parameter in the memory unit,
identifying at least one treatment portion of the user body from the image data and the at least one body parameter stored in the memory unit,
identifying at least one skin condition and/or at least one internal body condition, based on the at least one body parameter and the image data of the at least one treatment portion of the user body,
retrieving a treatment profile from the pre-stored data in the database of the memory unit based on the at least one external body skin condition and/or at least one internal body condition,
projecting light, from the light projection unit on the at least one skin condition and/or the at least one internal body condition according to the treatment profile retrieved from the memory unit, and
rotating the rotatable head synchronously in a direction of movement of the at least one treatment portion of the user body.

2. The device according to claim 1, wherein the camera is selected from a group of a normal optical camera, a thermographic camera, an infrared spectroscopy camera, an IP camera and a combination thereof, wherein the at least one sensor is selected from group of IR sensors, temperature sensors, thermal imaging sensor, ultrasonic and infrared sensors and the combination thereof.

3. The device according to claim 1, wherein the light projection unit includes a light direction controller, a light head and a light source, wherein the light source is a laser light, LEDs, photo reactive chemical producing light, phosphorus or any other suitable light source generating the light ranging from 100-1600 nm wavelength.

4. The device according to claim 1, wherein the processor is further enabled to utilize a localization module, an artificial intelligence module and machine learning module, and an object detection module and image processing module, in order to identify the at least one skin condition and/or the at least one internal body condition by using the at least one body parameter and the image data of the at least one treatment portion of the user body;
wherein the localization module is configured to deploy a pre-processing algorithm capable of segmenting an unstructured scene into objects using visual cues including shape, texture, edges, and color, in real time;
wherein the artificial intelligence and machine learning module is configured to generate predictive models from records of historical treatments provided to the user; and
wherein the object detection and image processing module is configured to identify specifically trained objects within the image data.

5. The device according to claim 1, wherein the processor is further enabled to compare the image data and the at least one body parameter of the user body with the pre-stored data to retrieve the treatment profile related to the at least one skin condition and/or the at least one internal body condition, wherein the treatment profile is having includes treatment information related to the at least one skin condition and/or the at least one internal body condition.

6. The device according to claim 1, wherein the device further comprises means configured to connect with a remote device for displaying the image data, the at least one treatment portion of the user body, at least one skin condition, at least one internal body condition, and the treatment information, and wherein, the remote device is adapted to send an input to the controller unit via wired or wireless communication means.

7. The device according to claim 1, wherein the at least one skin condition is selected from a group of skin disorder, skin problems, skin cancer, aged skin, dead skin, sun tanning, wounds, allergy, inflammation, dermatitis, hives, marks, acnes, redness, irritants, itching, swelling, sebaceous, lesions pimples, wrinkles and combination thereof.

8. The device according to claim 1, wherein the at least one internal body condition is selected from a group of blood flow, fever, erectile dysfunction, joints pain, muscles pain, grey hair, hair fall, eyebrows, cellular improvement, sleep disorder, jaundice, cancer, internal body problems, Medical condition and combination thereof.

9. The device according to claim 1, wherein the at least one treatment portion of the user body includes a face, hand, head, genital area, full body and any specific body portion having the at least one skin condition and/or the at least one internal body condition.

10. The device according to claim 1, wherein the device is configured to allow the user to select at least one of a type of treatment, treatment time, intensity of light projection and shape of a light projection based on his/her body condition.

11. The device according to claim 1, wherein the light projected from the light head is adapted to continuously follow the at least one treatment portion of the user body within a predefined distance.

12. The device for according to claim 1, wherein the device is configured to use a light therapy selected from a group consisting of LED light therapy, laser light therapy, Photo-bio-modulation therapy (PBMT), Photodynamic Therapy (PDT), UV based light therapy and a combination thereof.

13. The device according to claim 1, wherein the processor is further enabled to analyze a refractive index of the at least one treatment portion and project the light based on the refractive index of the at least one treatment portion, wherein the processor is further enabled to adjust focus of the light on the at least one treatment portion based on the refractive index in order to avoid falling of brightness and reflective light on the eyes of the user.

14. The device according to claim 1, wherein the processor is further enabled for:
generating and displaying a treatment report to the user, wherein the treatment report includes information regarding improvement after the light therapy performed on the at least one treatment portion of the user body.

15. The device according to claim 1, wherein the processor is further enabled to allow the user to manually perform the steps of:
identifying at least one treatment portion;
identifying the at least one skin condition and/or the at least one internal body condition; and
selecting the treatment profile or creating a new treatment profile based on the at least one skin condition and/or the at least one internal body condition.

16. The device as claimed in claim 1, wherein the camera is configured to receive a gestural input and the controlling unit is configured to activate the device on the receipt of the gestural input.

17. A system for providing light therapy to a user body, the system comprising:
a plurality of devices for providing light therapy to the user body, wherein each one of the plurality of devices includes:
a rotatable head including a light projection unit, a camera unit, and a memory unit operably connected with a controlling unit,
a first housing including a spindle adapted to rotate, wherein the rotatable head has been included in the first housing and mounted onto the spindle,
a second housing including a rotation unit, wherein the rotation unit includes a motor, wherein the first housing is mounted on the second housing,
wherein a first end of the spindle is connected with the motor and a second end of the spindle is connected with the rotatable head,
wherein the camera unit includes a camera and at least one sensor,
wherein the memory unit includes a database having a pre-stored data, wherein the pre-stored data is related to a plurality of skin conditions, a plurality of internal body conditions, a plurality of treatment profiles corresponding to the plurality of skin and internal body conditions, and a plurality of user profiles corresponding to a plurality of respective users;
wherein the controlling unit is operably connected to the camera unit, the memory unit, and the light projection unit, wherein the controlling unit includes a processor which is adapted to execute a computer implemented code stored in the memory unit, in order to control functionalities of the camera unit, the memory unit, and the light projection unit, the computer implemented code when executed by the processor, enables processor to perform following steps of:
scanning the user body, by the camera unit, to capture image data and at least one body parameter of the user body, wherein the camera is adapted to capture the image data and the at least one sensor is adapted to collect the at least one body parameter,
storing the image data and the at least one body parameter in the memory unit,
identifying at least one treatment portion of the user body from the image data and the at least one body parameter stored in the memory unit, identifying at least one external body skin condition and/or at least one internal body condition based on the at least one body parameter and the image data of the at least one treatment portion of the user body,
retrieving a treatment profile from the pre-stored data in the database of the memory unit based on the at least one external body skin condition and/or at least one internal body condition,
projecting light, from the light projection unit on the at least one skin condition and/or the at least one internal body condition according to the treatment profile retrieved from the memory unit, and
rotating the rotatable head synchronously in a direction of movement of the at least one treatment portion of the user body.

18. The system according to claim 17, wherein the plurality of devices are connected to each other via a wired or wireless communication means, wherein the plurality of respective controlling units is further enabled to synchronously allocate a plurality of separate treatment portions to the plurality of respective devices and prevent overlap of the light projected from the plurality of respective light projection units.

19. A method for providing light therapy to a user body, the method comprising:
receiving image data and at least one body parameter from a camera unit, wherein the camera unit includes a camera and at least one sensor, wherein the image data is captured by the camera, and the at least one body parameter is collected by the at least one sensor;
storing the image data and the at least one body parameter in a memory unit;
identifying at least one treatment portion of the user body from the image data and the at least one body parameter stored in the memory unit;
identifying at least one skin condition and/or at least one internal body condition based on the at least one body parameter and the image data of the at least one treatment portion of the user body;
retrieving a treatment profile from the memory unit based on the at least one skin condition and/or at least one internal body condition, wherein the memory unit includes a database having pre-stored data related to a plurality of skin conditions, a plurality of internal body conditions, a plurality of treatment profiles corresponding to the plurality of skin and internal body conditions, and a plurality user profiles corresponding to a plurality of respective users;
projecting light, from a light projection unit on the at least one skin condition and/or the at least one internal body condition according to the treatment profile retrieved from the memory unit;
wherein the camera unit, the memory unit and the light projection unit have been included in a rotatable head;
wherein the rotatable head has been included in a first housing and mounted onto a spindle; wherein the first housing is mounted on a second housing, wherein the second housing includes a rotation unit, wherein the rotation unit includes a motor;
wherein a first end of the spindle is connected with the motor and a second end of the spindle is connected with the rotatable head;
rotating the rotatable head synchronously in a direction of movement of the at least one treatment portion of the user body.

20. The system as claimed in claim 19, wherein the connection of the plurality of devices is configured as a master-slave model, wherein one of the plurality of devices is a master device and the other devices are slave devices, the controlling unit of the master device being configured to control the respective controlling units of the slave devices.

* * * * *